United States Patent
Richman

(10) Patent No.: US 9,179,978 B1
(45) Date of Patent: Nov. 10, 2015

(54) ORGANIZER FOR SURGICAL TOOLS AND ITEMS USED DURING SURGERY

(71) Applicant: Lawrence M. Richman, Los Angeles, CA (US)

(72) Inventor: Lawrence M. Richman, Los Angeles, CA (US)

(73) Assignee: Lawrence M. Richman, Los Angeles, CA (US)

( * ) Notice: Subject to any disclaimer, the term of this patent is extended or adjusted under 35 U.S.C. 154(b) by 0 days.

(21) Appl. No.: 14/509,986

(22) Filed: Oct. 8, 2014

(51) Int. Cl.
 B65D 83/10 (2006.01)
 A61B 19/02 (2006.01)

(52) U.S. Cl.
 CPC .................................. *A61B 19/0271* (2013.01)

(58) Field of Classification Search
 CPC ... A61M 5/002; A61M 5/008; A61B 19/0271
 USPC ......... 206/370, 210, 571, 366, 562, 563, 373, 206/369, 377, 355, 493, 494, 564, 477–483, 206/1.5, 459.1, 438; 211/70.6, 70.7
 See application file for complete search history.

(56) References Cited

U.S. PATENT DOCUMENTS

| | | | |
|---|---|---|---|
| 3,132,765 A | | 5/1964 | Florendo |
| 4,046,254 A | | 9/1977 | Kramer |
| 4,153,160 A | * | 5/1979 | Leigh ............................ 206/370 |
| 4,767,008 A | | 8/1988 | Warnecke et al. |
| 5,170,804 A | | 12/1992 | Glassman |
| 5,294,413 A | * | 3/1994 | Riihimaki et al. ............ 422/297 |
| 5,441,152 A | | 8/1995 | Estes |
| 5,505,916 A | * | 4/1996 | Berry, Jr. ....................... 422/300 |
| 6,230,888 B1 | | 5/2001 | Frieze et al. |
| 8,177,064 B2 | | 5/2012 | McCormick et al. |
| 2007/0023305 A1 | * | 2/2007 | Chan et al. .................... 206/366 |
| 2007/0095717 A1 | | 5/2007 | Tucker |
| 2010/0065456 A1 | * | 3/2010 | Junk et al. ..................... 206/363 |

OTHER PUBLICATIONS

Amiwelisten, "Surgical Instrument counting and organizational system," YouTube, Feb. 14, 2008, https://www.youtube.com/watch?v=Oyb7i7WafAo.

* cited by examiner

*Primary Examiner* — Luan K Bui
*Assistant Examiner* — Rafael Ortiz
(74) *Attorney, Agent, or Firm* — Michael D. Harris; SoCal IP Law Group LLP

(57) ABSTRACT

An organizer for holding surgical instruments includes a tray that has instrument wells extending from the top surface of the tray. The shape of each instrument well corresponds to particular surgical instrument's shapes. Each instrument well's depth corresponds to the height of a particular stack of surgical instruments. Pivoting locking bars extend over each instrument well to a locked position. In that position, instruments cannot be added to or removed from the instrument well. When the bar extends over the instrument well, the bar rests against the top instrument in the instrument well if the instrument well is full. If one or more instruments are missing from their instrument well, the locking bar's intersection with the structure of the tray adjacent the instrument well is such that an end of the locking bar projects about the tray's surface. Thus, one can notice quickly whether all instrument wells are full.

10 Claims, 6 Drawing Sheets

ORGANIZER FOR SURGICAL TOOLS AND ITEMS USED DURING SURGERY

BACKGROUND

1. Field

Organizers for holding surgical instruments in operating rooms.

2. General Background and State of the Art

Surgeons and their staff need their instrument and other items used during surgery to be readily accessible and well organized. Spending time looking for a clamp that other instruments hide adds crucial time to a surgery. That is undesirable for the patient because delays increase the length of the surgery and time under anesthesia.

Increasing the time for each surgery also is detrimental to surgeons, accompanying physicians and staff and to the hospital or surgical center. Surgeons and other physicians and staff are in high demand and often perform many procedures daily. Adding time to each surgery can eliminate one or more surgeries per day or force a surgery planned for one day to be delayed to the next or a later day.

For hospitals and surgical center, delays for each surgical team are compounded. The operating rooms at many hospitals are fully utilized. That fact alone causes delays in scheduling patients' surgeries. In addition, if some or all the operating rooms handle even one fewer procedures every day, the hospital becomes less efficient. Therefore, costs increase. Because fully equipped operating rooms are very expensive, adding more operating rooms is costly. On the other hand, having any added but under-utilized operating rooms generates less revenue to pay for the operating rooms or for other hospital expenses.

Increased costs and decreased efficiency are not the only concerns. At the end of each procedure, all instruments must be accounted for. For example, if the surgeon starts with 15 surgical clamps and has five unused surgical clamps left at the end of the surgery, the other ten must be accounted for. Otherwise a missing clamp might be inside the patient. More likely, it may be hidden on the operating table or dropped on the floor. Finding the clamps may not be difficult and may not take excessive time, but the time spent adds up for each operating room, each hospital and hospitals in general.

SUMMARY

An organizer for holding surgical instruments includes a tray that has indentations extending down from the top surface of the tray. The indentations form instrument wells. Each instrument well has a shape that corresponds to the shape of particular surgical instruments. For example, the instrument well for a scissors has two round regions to receive the scissors' finger openings, a rectangular region extending from the round regions and a narrow region corresponding to the scissors' pointed end. Likewise, the instrument well for scalpels has a tapered length corresponding to the handle and a narrower region for the blade.

The depth of each instrument well corresponds to the height of a stack of the surgical instruments that a surgeon plans to use. For example, if a particular surgery typically uses three scalpels, the depth of the scalpel instrument well would accommodate the three scalpels. If another type of surgery uses more than three scalpels, the instrument well would be deeper. Otherwise, more than one instrument well could be used with the scalpels divided between the wells.

The tops of the stack may be aligned with the tray's top surface or the stacks should be the same, short distance below that surface. After surgery, the used instruments are returned to their instrument well. Thus, at a glance, one can tell whether the instrument well is full. If any instrument wells are not full, an instrument is missing and must be found.

The tray may have locking bars at the upper surface of the tray, which extend over each instrument well. In that position, instruments cannot be added to or removed from the instrument well. The bar can pivot or otherwise move to a position uncovering the instrument well so that instruments can be the removed and added to the instrument well. When the bar extends over the instrument well, the bar will be against the top instrument in the instrument well if the well is full. Seeing that contact between the bar and the top instrument allows one to see immediately whether the instrument well is full. In the event that a surgical instrument is missing, the far end of the locking bar may be offset to project upwards to alert the operating staff of the missing instrument.

If the instruments are returned to their instrument well following surgery, each instrument well should contain the same number of instruments that filled the instrument well when the surgery started. If one or more instruments are missing from their instrument well, the locking bar's intersection with the structure of the tray adjacent the instrument well is such that an end of the locking bar projects about the tray's surface. Thus, one can notice quickly whether all instrument wells are full because all surgical instruments are returned to their indentation.

To assist the operating room staff further, part or all of the top of the locking bar may be colored green or another color so that when the locking bar in the closed position over the instruments, the surgeon or staff member can see that the bar is closed. Similarly, part or all of the opposite side of the locking bar may be colored red or another color different from the first side of the locking bar. Therefore, one will see red when the locking bare is in the open position when instruments are being used. At the end of the operation, the operating room staff can be assured that all instruments are accounted for when all the locking bars are fully flush with the tray and show green over each instrument well. Instead of color, the top and bottom of the locking bar may have contrasting symbols.

The locking bar's fulcrum may be positioned so that part of the bar sticks up if the instrument well is not full.

DETAILED DESCRIPTION

Figure 1:
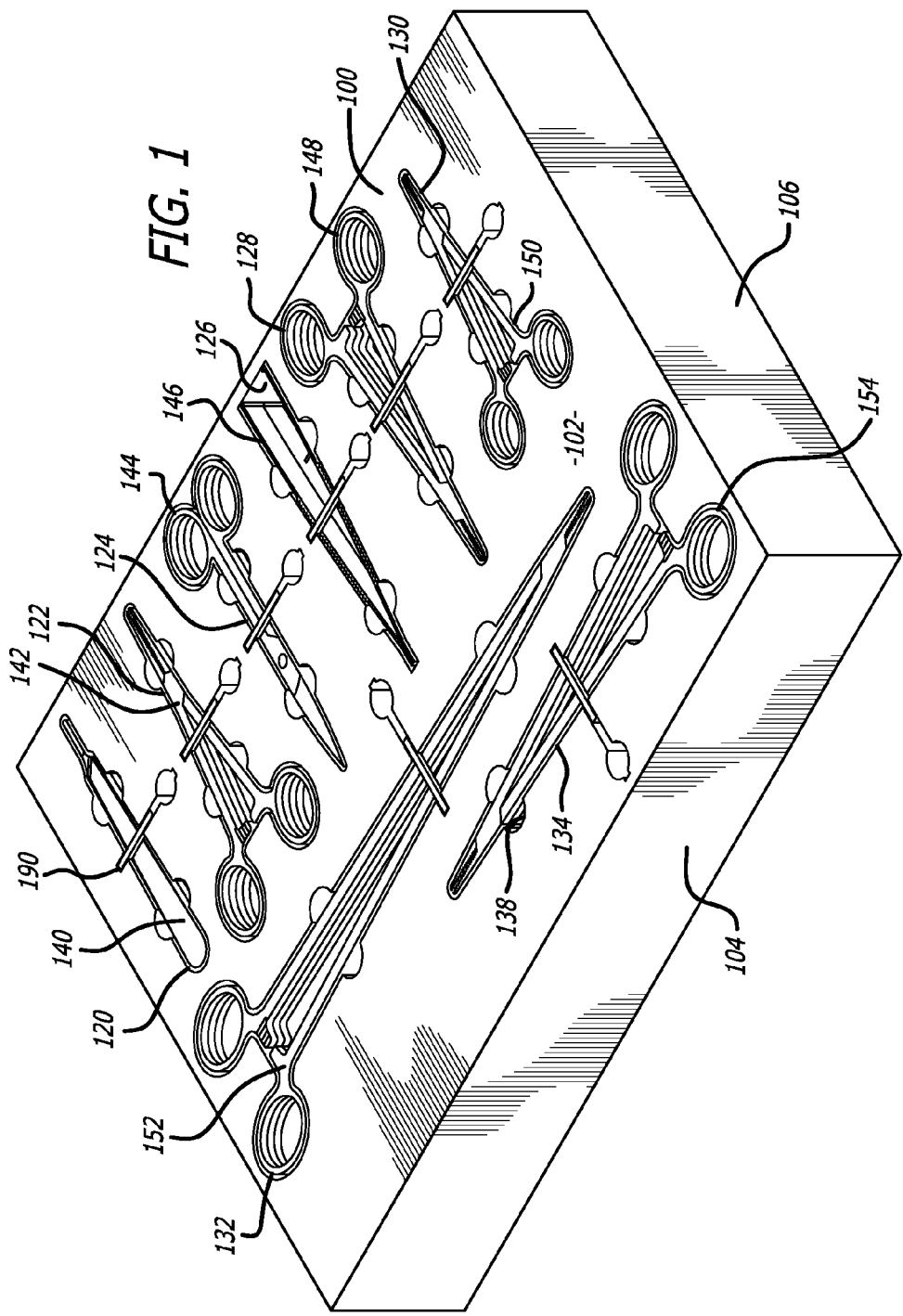
FIG. 1 is a perspective view of the tray showing instruments in the instrument wells

Tray 100 (FIGS. 1, 2 and 3) for holding surgical instruments may be made from any suitable material such as plastic or non-corrosive metal such as stainless steel, but cardboard, formed paper and composites are options. The nonmetal materials may be easier to form and are less costly than metal. The material for the tray shown in the drawings is rigid, but the material could be bendable.

Tray 100 may be disposable. However, non-disposable materials should be able to retain their form when subjected to autoclave temperatures (100° C. at 20 psi) or whatever temperatures and pressures are customary for a particular facility.

Tray 100 shown in the drawings has a top surface 102 and depending sidewalls, only three of the four, 104, 106 and 108, are visible in the drawings. The tray is rectangular, but other shapes such as polygons, circles, ellipses and other freeform shapes could be acceptable.

The base of tray 100 is open, but it could be closed. With the base open, one has access to the tray's underside 110 (FIG. 3).

Top surface 102 of tray 100 has several indentations that form instrument wells for receiving surgical instruments. Eight instrument wells, 120, 122, 124, 126, 128, 130, 132 and 134, are shown in the drawings, but the tray could have more or fewer instrument wells. Rather than adding many instrument wells to make a tray that may be too large, two or more trays of a desired size could replace a single, large tray.

Figure 2:
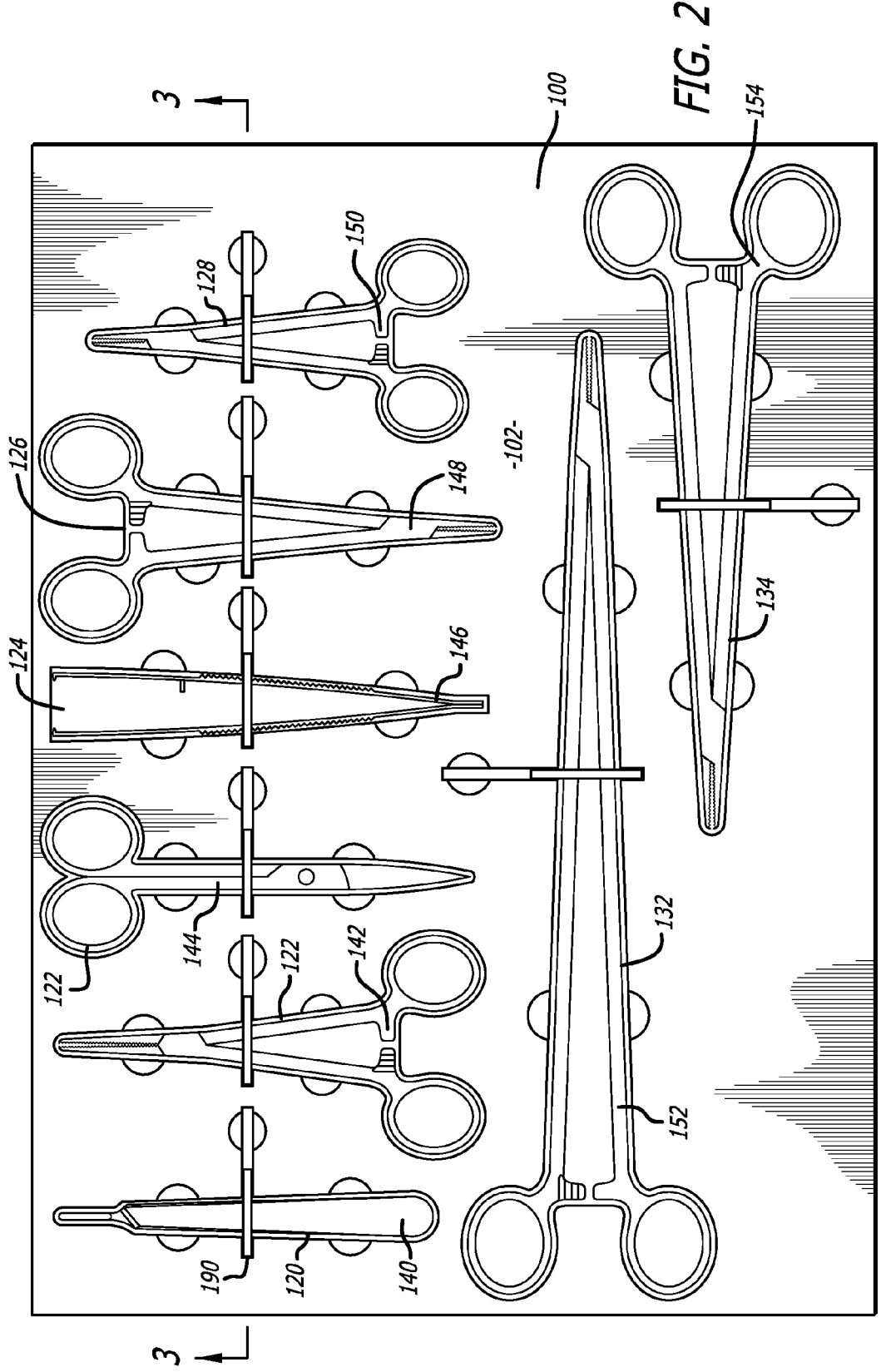
FIG. 2 is a plan view of the tray showing instruments in the instrument wells.

Each instrument well is shaped to receive a particular instrument. For example, well 120 is shaped to receive scalpels 140 (FIGS. 1 and 2). Instrument well 122 receives surgical clamps 142. Scissors 144 fit into instrument well 144, and forceps 146 fit into instrument well 126. Well 128 holds more clamps 148. Small, medium and large needle holders 150, 154 and 152 are received in wells 130, 134 and 132, respectively. The instrument wells may have depressions 138 at appropriate places to allow easier gripping of an instrument.

Figure 3:
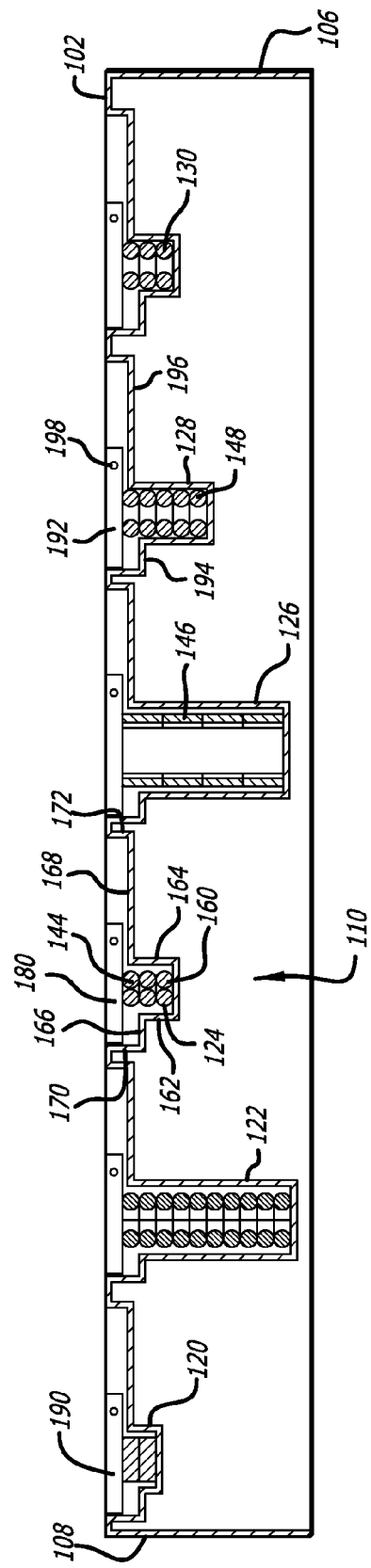
FIG. 3 is a side, sectional view of the tray taken through plane 3-3 of FIG. 2.

FIG. 3 shows that the instrument well may have different depths to accommodate different sizes and numbers of surgical instruments. For example, consider instrument well 124 in FIG. 3, which receives scissors 144. The indentation that forms the instrument well includes base 160, which depends from sidewalls 162 and 164. The tops of the sidewalls intersect shoulders 166 and 168, and the outside of each shoulder intersects short extension 170 and 172. The extensions intersect top surface 102 of tray 100. The functions for the space above the shoulders are discussed below.

Experienced surgeons anticipate that they will use a specific number of each surgical instrument for a specific surgery. Accordingly, the number of instrument wells and their shapes for particular instruments could vary for specific surgeries.

Consider a surgeon who anticipates for a particular procedure needing three scissors of the size of scissors 144 in FIG. 1. Thus, for that surgery, the instrument well is deep enough to hold three scissors—no more and no fewer. Similarly, if the surgeon anticipates needing four forceps, instrument well 126 is deep enough to hold four forceps 146. Because the forceps are thicker than the thickness of scissors 144, the instrument well 126 holding four forceps is much deeper than the instrument well 124 holding three scissors. The deepest instrument well, 122, holds ten surgical clamps 142.

A leaf or other spring (not shown) could be used at the bottom of some or all the instrument wells to urge the instruments upward. Such an arrangement could assist in gripping the top-most instrument.

Figure 4:
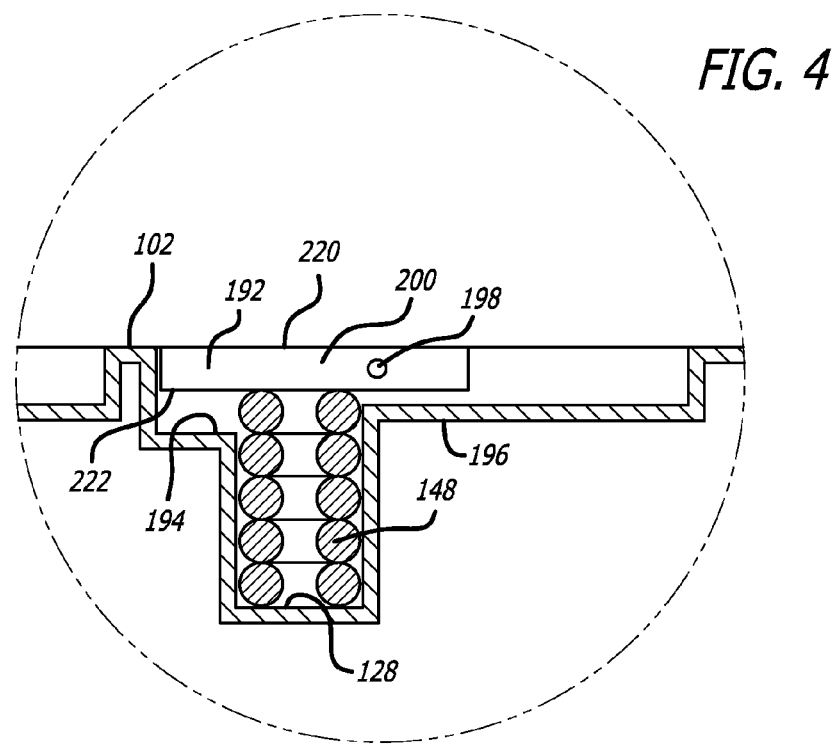
FIGS. 4 and 5 are sectional views of one instrument well at the tray's top surface.

A locking bar extends over the top-most instrument in each instrument well. The locking bars are similar; only locking bars 190 and 192 are discussed. Instrument well 128 holds five forceps or surgical clamps 148 (FIG. 4). Locking bar 192 mounts on pin 198 in the space above shoulders 194 and 196. The locking bar's top face 200 is in the same plane as top surface 102 of tray 100. The locking bar is seen resting on the upper-most forceps in FIG. 4.

Figure 6:
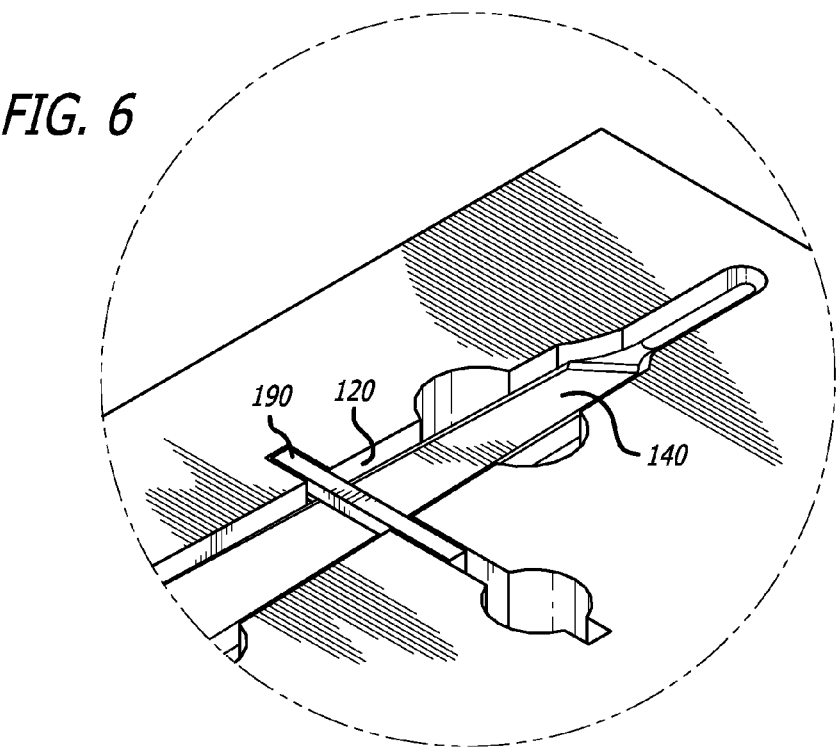
FIGS. 6, 7, 8 and 9 are perspective views of one instrument well at the tray's top surface showing the locking bar in different orientations.
Figure 7:
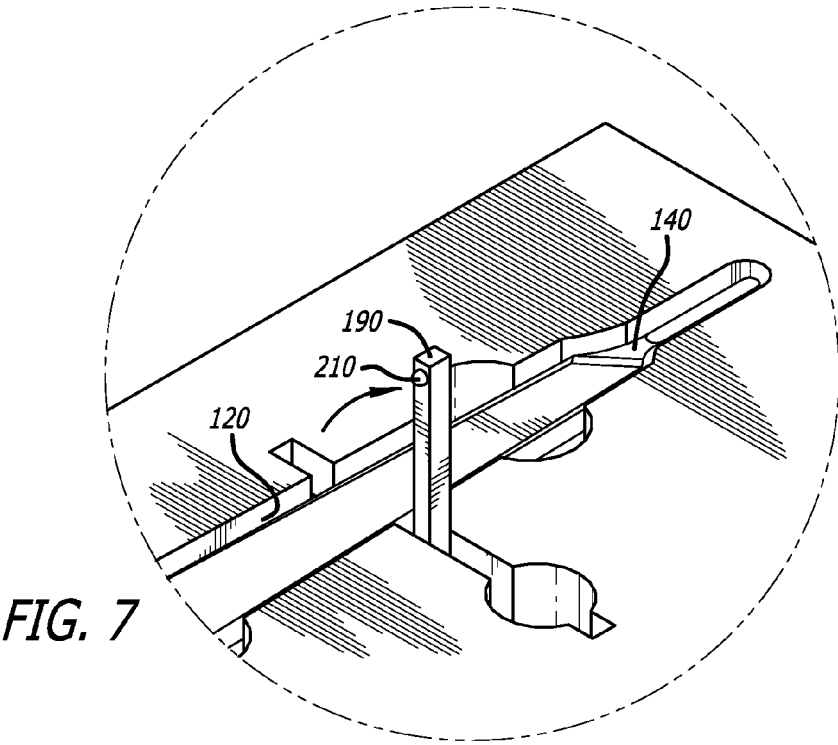
Figure 8:
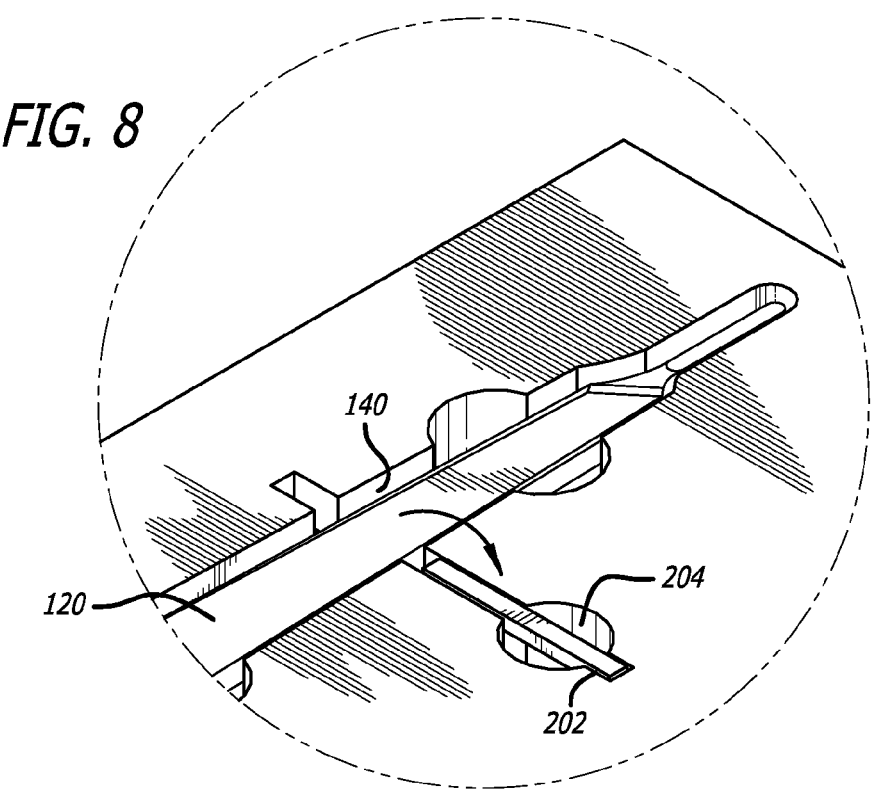

To remove an instrument from an instrument well, the locking bar is pivoted to or past vertical. Thus, as FIGS. 6 and 7 show, locking bar 190 pivots about its pin (not shown) from the horizontal position over instrument well 120 and scalpels 140 (FIG. 6) to a vertical orientation (FIG. 7). The locking bar can continue to rotate to the FIG. 8 position where it rests in groove 202. In that position (and it the FIG. 6 position), a person moving his or her hand over the top 102 of tray 100 will not encounter any obstructions. The groove also may have depressions 204 that allow insertion of a finger or tool to pull the locking bar out of the groove. The locking bars may have a spring-loaded pin 210 that engages a detent (not shown) in the groove. That arrangement tends to hold the locking bar over the instruments until one rotates the locking bar away from the instruments.

Figure 5:
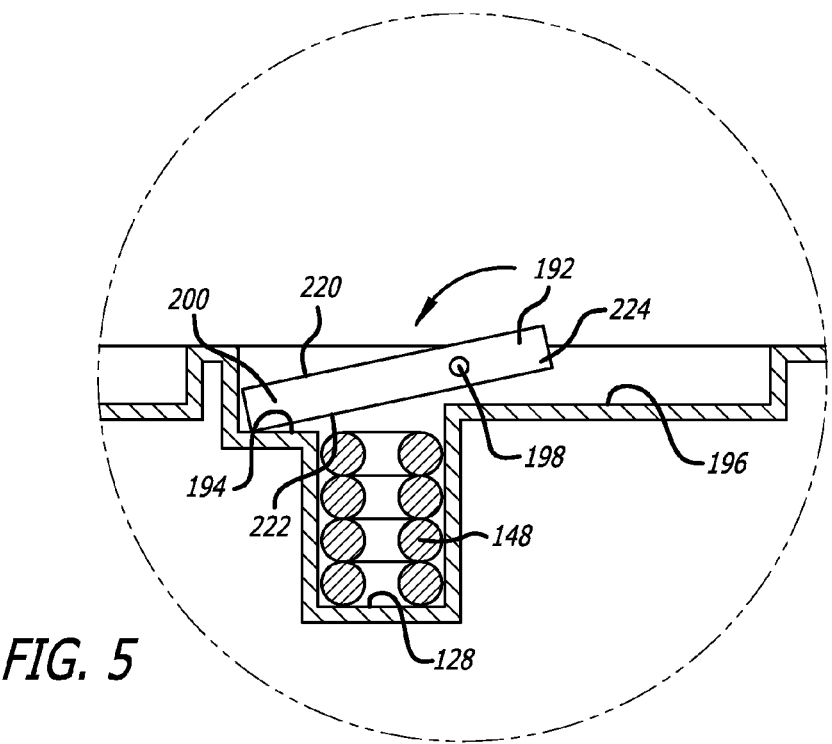

The locking bar may have different colors on its top and bottom. All or part of top face 220 (FIG. 4) could be colored green, for example, which would show that all locking bars are in their locked or almost locked (FIG. 5) position. All or part of bottom face could be colored red, for example, so that the red face would show when the locking bar is open to allow access to instrument well 148. Symbols could replace the colors.

In the drawings, the locking bars pivot over and away from the instrument wells. Other arrangements are possible although they may not offer all the advantages of the pivoting locking bars. For example, the locking bar could slide in an elongated groove from a position over the instrument well to a position spaced from the instrument well. Likewise, a U-shaped fastener could be inserted into openings adjacent the sides of each instrument well. Other arrangements also are possible.

When the surgery begins, the surgeon or assistant opens all the locking bars, e.g., bars 190 and 200, of fully loaded tray 100. Of course, not all locking bars must be opened in the beginning, but doing so may be more convenient. As the surgery proceeds, the surgeon and his or her staff use the instruments as necessary until the surgery is finished. Then the instruments are returned to their original instrument well.

When all five forceps or surgical clamps 148 are returned to instrument well 128 and locking bar 200 is pivoted to its lock position, the locking bar aligns with the top surface 102 of tray 100. See FIG. 4. However, if only four clamps are returned to their instrument well, when the locking bar is pivoted to the lock position, the end of the locking bar continues until it contacts shoulder 194. See FIG. 5. The right side of the locking bar (FIG. 5) projects above the top surface of the tray. That is because pin 198, which acts as a fulcrum is closer to the short side 224 of the locking bar. Thus, one knows at a glance or by running a hand over the tray that at least one forceps is missing from its instrument well.

Figure 9:
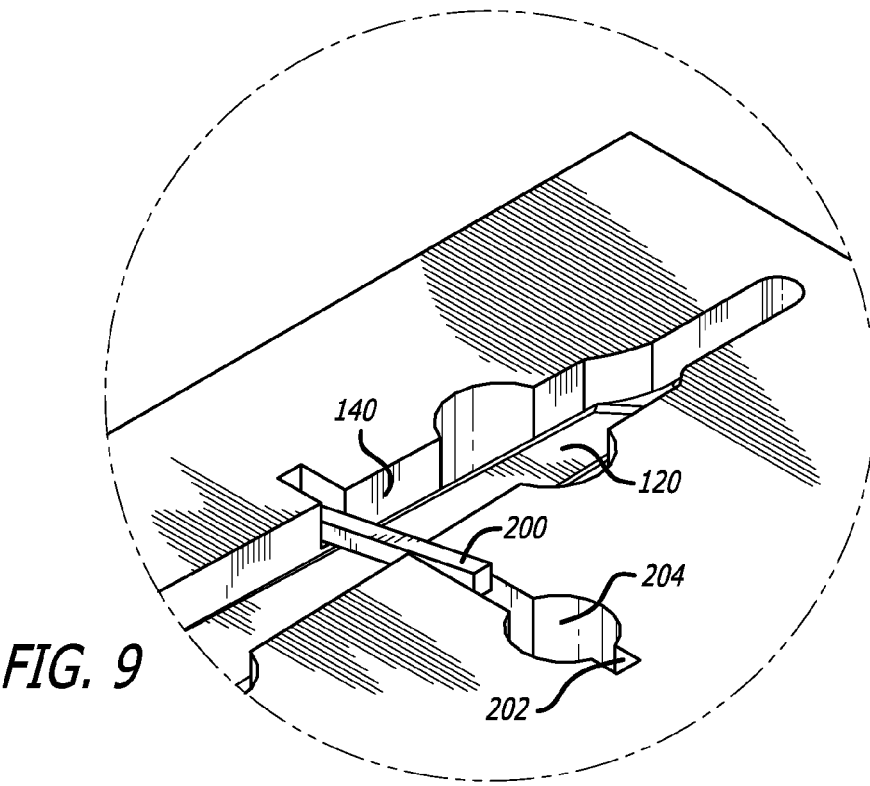

Likewise, if fewer than two scalpels 140 are returned to instrument well 120, locking bar 200 will not be flat. See FIG. 9. One can easily tell that at least one scalpel is missing.

Thus, one advantage of having pivoting locking bars such as bars 190 or 200 is their orientation projecting above surface 102 of tray 100 when the instrument well is not full. Upon finding a tool missing from the tray, those in the operating room can search for the tool. Because the search is part of the time spent returning the instruments to the tray, locating all the instruments used is handled at one time and becomes more efficient.

The description is illustrative, not limiting and is by way of example only. Although this application shows and describes examples, those having ordinary skill in the art will find it apparent that changes, modifications or alterations may be made. Many of the examples involve specific combinations of method, act or system elements, but those acts and elements may be combined in other ways to accomplish the same objectives. Acts, elements and features discussed only in connection with one embodiment are not intended to be excluded from a similar role in other embodiments.

"Plurality" means two or more. A "set" of items may include one or more of such items. The terms "comprising," "including," "carrying," "having," "containing," "involving," and the like in the written description or the claims are open-ended, i.e., each means, "including but not limited to." Only the transitional phrases "consisting of" and "consisting essentially of" are closed or semi-closed transitional phrases with respect to claims. The ordinal terms such as "first," "second," "third," etc., in the claims to modify a claim element do not by themselves connote any priority, precedence, or order of one claim element over another or the temporal order in which acts of a method are performed. Instead, they are used merely as labels to distinguish one claim element having a certain name from another element having a same name (but for use of the ordinal term). Alternatives such as "or" include any combination of the listed items.

I claim:

1. An organizer for holding surgical instruments comprising:
   a tray having an upper surface;
   a plurality of indentations in the tray forming instrument wells having a shape corresponding to the outer shape of surgical instruments;
   each instrument well configured to have a depth corresponding to the height of a stack of a predetermined number of such instruments, at least one instrument well being deeper than at least one other instrument well;
   wherein the depth of each instrument well holds a predetermined number of a particular tool, the organizer further comprising at least one first locking bar at the upper surface of the tray and mounted for movement between a first position covering a portion of a first instrument well to a second position uncovering the first instrument well, the first instrument well having at least one shoulder extending away from the first instrument well, the shoulder being positioned a distance below the upper surface of the tray such that the first locking bar is aligned with the upper surface when the first instrument well contains the predetermined number of a particular tool, the first locking bar being out of alignment with the upper surface when the first instrument well contains fewer or more than the predetermined number of a particular tool; and
   wherein the first locking bar is pivotably mounted on a pin, the first locking bar having a short section extending from the pin and a longer section opposite the short section, the pin acting as a fulcrum and projecting the short section of the first locking bar above the pin when the first locking bar is returned to first position and its corresponding instrument well contains fewer than the predetermined number of a particular tool.

2. The organizer of claim 1 wherein the first locking bar has upper and lower faces, the faces being of different colors.

3. The organizer of claim 1 wherein the first locking bar has upper and lower faces, the faces having different indicia.

4. The organizer of claim 1, wherein the upper surface of the tray is generally flat.

5. The organizer of claim 1, wherein the tray is generally rigid.

6. The organizer of claim 1, further comprising at least a second locking bar at the upper surface of the tray, adjacent a second instrument well, the second instrument well being spaced apart from the first instrument well, the second locking bar being mounted for movement between a first position covering a portion of the second instrument well to a second position away from the second instrument well, whereby the second locking bar in the first position blocking the removal and addition of a tool out of or into the second instrument well and whereby the locking bar in the second position allowing the removal and addition of a tool out of or into the second instrument well.

7. An organizer for holding surgical instruments having particular shapes and heights comprising:
   a plurality of indentations forming instrument wells, each instrument well having a top, the instrument wells extending downward from their respective tops, each instrument well having a shape corresponding to the outer shape of a particular surgical instrument;
   each instrument well configured to have a depth corresponding to the height of a stack of a particular instrument, at least one instrument well having a depth different from the depth of at least one other instrument well;
   and wherein the depth of each instrument well holds a predetermined number of a particular instrument, the organizer further comprising at least one first locking bar adjacent the top of a first instrument well and mounted for movement between a first position covering a portion of the first instrument well to a second position uncovering the first instrument well, the indentation forming a first instrument well having at least one shoulder extending away from the first instrument well, the shoulder being positioned a distance below the top of the first instrument well such that the locking bar is aligned with the top of the first instrument well when the first instrument well contains the predetermined number of a particular instrument, the first locking bar being out of alignment with the top of the first instrument well when the first instrument well contains fewer or more than the predetermined number of a particular instrument; and
   wherein the locking bar has upper and lower faces, the faces being of different colors.

8. The organizer of claim 7 wherein the first locking bar mounts for pivoting on a pin, the pin dividing the first locking bar into two unequal lengths of a shorter and longer section, the pin acting as a fulcrum and projecting the short section of the first locking bar above the pin when the first locking bar is returned to first position and its corresponding instrument well contains fewer than the predetermined number of a particular instrument.

9. The organizer of claim 7, further comprising at least a second locking bar at the upper surface of the tray, adjacent a second instrument well, the second instrument well being spaced apart from the first instrument well, the second locking bar being mounted for movement between a first position covering a portion of the second instrument well to a second position away from the second instrument well, whereby the second locking bar in the first position blocking the removal and addition of a tool out of or into the second instrument well and whereby the locking bar in the second position allowing the removal and addition of a tool out of or into the second instrument well.

10. An organizer for holding surgical instruments having particular shapes and heights comprising:
   a plurality of indentations forming instrument wells, each instrument well having a top, the instrument wells extending downward from their respective tops, each instrument well having a shape corresponding to the outer shape of a particular surgical instrument;
   each instrument well configured to have a depth corresponding to the height of a stack of a particular instrument, at least one instrument well having a depth different from the depth of at least one other instrument well; and wherein the depth of each instrument well holds a predetermined number of a particular instrument, the organizer further comprising at least one first locking bar adjacent the top of a first instrument well and mounted for movement between a first position covering a portion of the first instrument well to a second position uncovering the first instrument well, the indentation forming a first instrument well having at least one shoulder extending away from the first instrument well, the shoulder being positioned a distance below the top of the first instrument well such that the first locking bar is aligned with the top of the first instrument well when the first instrument well contains the predetermined number of a particular instrument, the first locking bar being out of alignment with the top of the first instrument well when the first instrument well contains fewer or more than the predetermined number of a particular instrument; and wherein the first locking bar has upper and lower faces, the faces having different indicia.

\* \* \* \* \*